United States Patent [19]

Engel

[11] 4,243,677
[45] Jan. 6, 1981

[54] INSECTICIDAL PERHALOALKYLVINYLCYCLO-PROPANECARBOXYLATES

[75] Inventor: John F. Engel, Medina, N.Y.

[73] Assignee: FMC Corporation, Philadelphia, Pa.

[21] Appl. No.: 65,257

[22] Filed: Jul. 30, 1979

Related U.S. Application Data

[63] Continuation of Ser. No. 927,198, Jul. 24, 1978, abandoned, which is a continuation-in-part of Ser. No. 870,973, Jan. 20, 1978, abandoned.

[51] Int. Cl.³ .................... A01N 53/00; C07C 79/22
[52] U.S. Cl. .................... 424/305; 260/326 A;
260/340.5 R; 260/347.2; 260/347.4; 260/464;
260/465 D; 260/544F; 260/544 L; 424/274;
424/275; 424/282; 424/285; 424/304; 424/308;
542/426; 542/429; 549/65; 549/66; 549/77;
549/79; 560/8; 560/18; 560/51; 560/83;
560/118; 560/124; 562/405; 562/432; 562/459;
562/500; 562/506
[58] Field of Search ............ 260/326 A, 340.5 R,
260/465 D; 560/18, 118, 124, 8; 424/304, 305,
306, 307, 308

[56] References Cited

U.S. PATENT DOCUMENTS

| 3,647,857 | 3/1972 | Morgan | 260/468 P |
| 4,024,163 | 5/1977 | Elliott et al. | 260/347.4 |
| 4,183,948 | 1/1980 | Huff | 424/304 |

FOREIGN PATENT DOCUMENTS 858137 2/1978 Belgium .
863151 7/1978 Belgium .
14749 2/1977 Japan .

OTHER PUBLICATIONS

Abstract No. 75226S for Japanese Pat. No. 7,140,617 published 12-1971.
Abstract No. 75227S for Japanese Pat. No. 7,140,618 published 12-1971.
Abstract No. 14873S for Japanese Pat. No. 7,106,918 published 2-1971.

Primary Examiner—Richard Raymond
Attorney, Agent, or Firm—Robert L. Andersen; H. Robinson Ertelt

[57] ABSTRACT

Perhaloalkylvinylcyclopropanecarboxylates having the general formula

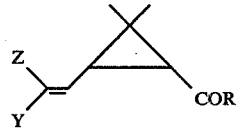

I are disclosed wherein one of Y and Z is a perhaloalkyl group. Compounds in which R is hydroxy, halogen or lower alkoxy are novel intermediates for preparation of insecticidal esters in which R is —OR¹ where R¹ is a wide variety of alcohol residues. The insecticidal efficacy and preparation of the compounds and intermediates therefor are described and exemplified.

3 Claims, No Drawings

INSECTICIDAL PERHALOALKYLVINYLCYCLOPROPANECARBOXYLATES

This is a continuation of application Ser. No. 927,198, filed July 24, 1978, now abandoned, which in turn is a continuation in part of U.S. Ser. No. 870,973, filed Jan. 20, 1978, now abandoned.

The present invention is directed to a novel class of cyclopropanecarboxylate insecticides, to intermediates therefor, and to an insecticidal method and composition. More particularly, the invention is directed to the insecticidal perhaloalkylvinylcyclopropanecarboxylates set forth in Formula I and to intermediates for these compounds.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott et al. of certain highly active compounds, for example, dihalovinylcyclopropanecarboxylates such as permethrin, the common name for 3-phenoxybenzyl 3-($\beta$,$\beta$-dichlorovinyl)-2,2-dimethylcyclopropanecarboxylate. This class of compounds, set forth in U.S. Pat. No. 4,024,163, issued May 17, 1977, exhibits substantially improved photostability when compared with previously available cyclopropanecarboxylates such as the chrysanthemamates, i.e., compounds of formula I in which Y and Z are each methyl.

The prior art cyclopropanecarboxylates such as those described in the foregoing U.S. Patent have shown high levels of activity against insects of the Order Lepidoptera, but many have not shown commercially satisfactory levels of activity against insects of the Order Homoptera, for example, aphids.

The present invention provides a new class of insecticidal cyclopropanecarboxylates, perhaloalkylvinylcyclopropanecarboxylates, generally exhibiting a high level of insecticidal activity, improved activity against insects of the Order Homoptera, such as aphids, and improved photostability.

The present invention also provides novel insecticidal compositions of the foregoing compounds, a method of controlling insects, and novel intermediates for the insecticidal compounds and compositions.

In this application, the term "lower", as applied to an alkyl group means having 1 to 6 carbon atoms, preferably 1 to 4 carbon atoms. The term "halo" or "halogen" means bromine, chlorine, or fluorine. With respect to a perhaloalkyl group the halogens may be the same or different and are suitably selected from fluorine and chlorine with fluorine being preferred. These definitions are applicable throughout the specification and claims except where a contrary meaning is clearly indicated.

The insecticidal compounds of this invention are cyclopropanecarboxylates of the general formula

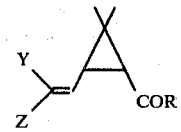

wherein one of Y and Z is a perhaloalkyl group having 1 to 4 carbon atoms, preferably 1 to 2 carbon atoms, and the other is hydrogen, halogen, lower alkyl, phenyl, phenylthio, or benzyl, with the proviso that Y and Z may be combined to form a perhalocyclopentylidene group, preferably a perfluorocyclopentylidene group. Particularly desirable compounds are trihalopropenyl, preferably trifluoropropenyl, cyclopropanecarboxylates of formula I in which one of Y and Z is trihalomethyl, preferably trifluoromethyl, and the other is halogen.

R is —OR$^1$ where —OR$^1$ represents a wide variety of alcohol residues which form insecticidal esters when combined with chrysanthemic acid [3-(2,2-dimethylvinyl)-2,2-dimethylcyclopropanecarboxylic acid] or the dihalovinylcyclopropanecarboxylic acids of U.S. Pat. No. 4,024,163 such as permethrin. That patent points out at column 3, lines 18 through 21, that the corresponding alkyl esters are "not insecticidal", and lists, (for instance at column 2, line 5 through column 3, line 17, and in Example 18) groups (i.e. alcohol residues) which form insecticidal esters when combined with the dihalovinylcyclopropanecarboxylic acids, or other vinyl or substituted vinyl cyclopropanecarboxylic acids. R$^1$ thus represents a group useful in the cyclopropanecarboxylate insecticide art to produce insecticidally active esters when combined with an appropriate known pyrethroid acid. For instance R$^1$ may be allethrolonyl, tetrahydrophthalimidomethyl, or may be represented by the formula

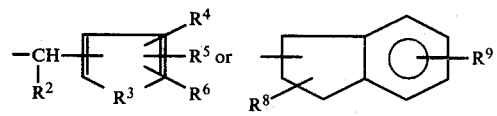

in which R$^2$ is hydrogen, lower alkyl, ethynyl, cyano, or trihalomethyl; R$^3$ is divalent oxygen, divalent sulfur, or vinylene; R$^4$, R$^5$, and R$^6$ are independently hydrogen, lower alkyl, halogen, lower alkenyl, phenyl, phenoxy, benzyl, phenylthio, or any two of R$^4$, R$^5$, and R$^6$ are joined to form a divalent methylenedioxy group attached to two adjacent ring carbon atoms of a phenyl ring, with the proviso that when R$^4$, R$^5$, or R$^6$ contains a phenyl ring such phenyl ring may be substituted with one to three substituents selected from halogen and lower alkyl; R$^8$ is hydrogen, lower alkyl, lower alkoxy, lower alkenyl, lower alkenyloxy, phenyl or benzyl; R$^9$ is hydrogen, halogen, lower alkyl, lower alkoxy, lower alkenyl, lower alkenyloxy, lower alkylthio, lower alkylsulfinyl, lower alkylsulfonyl, phenyl, phenoxy, benzoyl, nitro or cyano.

Of these alcohol residues, those in which R$^1$ is 3-phenoxybenzyl, α-cyano-3-phenoxybenzyl, 3-phenylbenzyl, or 5-benzyl-3-furylmethyl are either readily available or easily and inexpensively synthesized from readily available starting materials. Moreover, compounds of formula I containing these alcohol residues in combination with an acid component in which one of Y and Z is trihalomethyl, preferably trifluoromethyl, and the other is halogen exhibit unexpectedly high activity against insects in general, remarkable efficacy against aphids, and, with the exception of 5-benzyl-3-furylmethyl, unusual photo-stability.

The insecticidal compounds and certain intermediates of this invention exist as cis and trans geometrical isomers; the carboxy and substituted vinyl groups at the 1 and 3 positions of the cyclopropane ring are either cis or trans with respect to each other. Preparation of such compounds will usually yield a mixture of cis and trans isomers, designated cis,trans, in which the ratio of cis to trans may vary over a wide range. For purposes of this specification the designations cis and trans are assigned in accordance with P. E. Burt, et al., *Pestic. Sci.*, 5 791–799 (1974). The compounds of this invention may also exist as E or Z isomers or as mixtures of E and Z isomers, designated E,Z, depending on the spatial relationship of substituents on the α-carbon of the vinyl group to those of the β-carbon of the vinyl group.

In the cyclopropanecarboxylate art it is known there may be substantial differences in the level of insecticidal activity between the cis and trans isomers. In general, as between the cis and trans isomer of a given cyclopropanecarboxylate, one isomer is usually more active than the other isomer and also more active than the cis,trans mixture. With respect to the present compounds the cis isomer is usually the more active. Similar differences in activity may also occur with respect to the E and Z isomers.

Unless a contrary intent is expressed, the invention embodies and includes all compounds in which the carboxy and substituted vinyl groups at the 1 and 3 positions of the cyclopropane ring are cis or trans, or a mixture of cis and trans configuration with respect to each other. Similarly, while the invention is illustrated with a mixture of the E and Z isomers, the individual isomers, as well as the mixtures, are also contemplated by and within the scope of the present invention. The enantiomers of these isomers are also included within the scope of the invention.

The compounds may be prepared from novel alkanoates of the formula

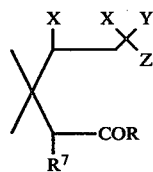

II in which one of Y and Z are defined as above; R is lower alkoxy, such as methoxy or ethoxy; $R^7$ is hydrogen, lower alkylcarbonyl, lower alkoxycarbonyl, or cyano, preferably hydrogen; and X is chloro or bromo. Example 1 illustrates a method for preparation of the preferred intermediates of Formula II by reacting together a lower alkyl 3,3-dimethyl-4-pentenoate and a compound of the formula $X_2$—C(Y) (Z) where X, Y, and Z are as defined above.

This alkanoate is then coverted to a novel compound of the formula

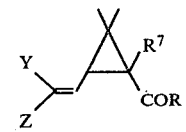

III in which R is lower alkoxy, hydroxy or halogen and Y,Z and $R^7$ are as defined above, for example, by dehydrohalogenating the compound of formula II. This reaction may take place in steps via the intermediates

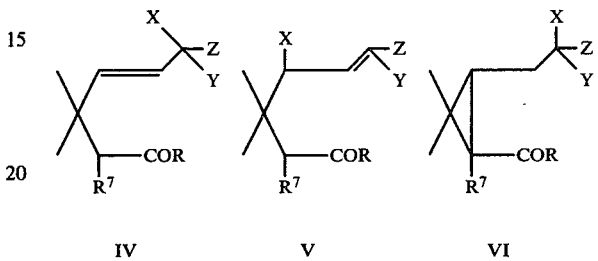

IV      V      VI and may be conducted in a single step by removal of 2 halogens or stepwise. These intermediates or mixtures of these may be recovered if desired. The compound of formula III is then converted to the compound of formula I by methods known to the art, for example, by removing $R^7$ (if other than hydrogen) and transesterifying with $HOR^1$. Other methods for converting R to $-OR^1$ are well known in the art.

The examples which follow illustrate preparation of the insecticidal compounds and novel intermediates therefor in accordance with the general method described above. In the examples all temperatures are in degrees centigrade, all pressures are in mm. Hg, and reduced pressure for concentration of liquid is produced by a water aspirator unless otherwise specified.

Example 1 illustrates the preparation of compounds of formula II.

EXAMPLE 1

Synthesis of Ethyl 3,3-Dimethyl-4,6,6-Trichloro-7,7,7-Trifluoroheptanoate

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure.

Additional intermediates of formula II, prepared in accordance with the method illustrated in Example 1, are set forth in Table I.

Examples 2 and 3 illustrate preparation of the lower alkyl esters of formula III. Example 2 is a two-step process via the intermediate of formula VI. Example 3 is a one-step process.

EXAMPLE 2

Synthesis of Methyl Cis,Trans-3-[2-Chloro-3,3,3-Trifluoropropenyl]-2,2-Dimethylcyclopropanecarboxylate

A. Preparation of methyl cis,trans-3-[2,2-dichloro-3,3,3-trifluoropropyl]-2,2-dimethylcyclopropanecarboxylate as an intermediate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to −5° C. To the stirred solution was added dropwise a solution of 16.4 grams (0.14 mole) of potassium tert-butoxide in 200 ml of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 g of methyl cis,-trans-3-[2,2-dichloro-3,3,3-trifluoropropyl]-2,2-dimethylcyclopropanecarboxylate; b.p. 55°–57° C./0.09 mm Hg. The ir and the nmr spectra were consistent with the proposed structure.

Elemental analysis calc'd for $C_{10}H_{13}Cl_2F_3O_2$: C40.98; H4.47; Found: C41.50; H4.41

B. Synthesis of methyl cis,trans-3-[2-chloro-3,3,3-trifluoropropenyl]-2,2-dimethylcyclopropanecarboxylate.

A stirred solution of 30.6 g (0.105 mole) of methyl cis,trans-3-[2,2-dichloro-3,3,3-trifluoropropyl]2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous solution saturated with sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl cis,trans-3-[2-chloro-3,3,3-trifluoropropenyl]-2,2-dimethylcyclopropanecarboxylate; b.p. 40°–60° C./0.05 mm. The ir and the nmr spectra were consistent with the proposed structure. The nmr spectra indicated an 88:12 mixture of cis:trans isomers.

Analyses calc'd for $C_{10}H_{12}ClF_3O_2$: C 46.80; H 4.71; Found: C 46.91; H 4.79.

EXAMPLE 3

Synthesis of Ethyl Cis,Trans-3-[2-Chloro-3,3,3-Trifluoropropenyl]-2,2-Dimethylcyclopropanecarboxylate To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl cis,trans-3-[2-chloro-3,3,3-trifluoropropenyl]-2,2-dimethylcyclopropanecarboxylate. The nmr and the ir spectra were consistent with the assigned structure and indicated the product was a mixture of approximately equal parts of cis and trans isomers.

Additional intermediates of formula VI, prepared in accordance with the method illustrated in Example 2A, are set forth in Table II.

Additional lower alkyl esters of formula III, prepared in accordance with Example 2 or Example 3 above, are set forth as Compounds 3.1 to 3.8 of Table III. Compounds 3.1 through 3.7 were prepared in accordance with Example 2. Compound 3.8 was prepared in accordance with Example 3.

EXAMPLE 4

Synthesis of Trans and Cis,Trans-3-[2-Chloro-3,3,3-Trifluoropropenyl]-2,2-Dimethylcyclopropanecarboxylic Acid A solution of 16.2 g (0.06 mole) of ethyl cis,trans-3-[2-chloro-3,3,3-trifluoropropenyl]-2,2-dimethylcyclopropanecarboxylate in 94 ml (0.078 mole) of a stock solution containing 3.34 g of sodium hydroxide, 94 ml of ethanol and 6 ml of water was stirred while heating under reflux for a period of 18 hours. The reaction mixture was concentrated under reduced pressure, 25 ml of water was added, and the mixture was acidified to pH1 using 6 N hydrochloric acid. The acifified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°–103° C. Concentration of the mother liquor provided a second fraction of solid weighing 0.8 g, m.p. 96°–103° C. Nmr spectra of the two fractions indicated the solids were each trans-3-[2-chloro-3,3,3-trifluoropropenyl]-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of solid, m.p. 64°–74° C. An nmr spectrum indicated the solid was a 50/50 mixture of cis and trans isomers of 3-[2-chloro- 3,3,3-trifluoropropenyl]-2,2-dimethylcyclopropanecarboxylic acid.

Additional free acids of formula III, prepared in accordance with Example 4, are set forth as Examples 4.1 through 4.7 of Table III.

EXAMPLE 5

Synthesis of Trans-3-[2-Chloro-3,3,3-Trifluoropropenyl]-2,2-Dimethylcyclopropanecarbonyl Chloride To a stirred solution of 4.1 g (0.0173 mole) of trans-3-[2-chloro-3,3,3-trifluoropropenyl]-2,2-dimethylcyclopropanecarboxylic acid in 40 ml of toluene at ambient temperature was added 1.7 g (0.022 mole) of pyridine, then 2.6 g (0.022 mole) of thionyl chloride in 25 ml of toluene. Upon complete addition the reaction mixture was stirred at ambient temperature for 17 hours. The reaction mixture was filtered through diatomaceous earth, and the filtrate was evaporated under reduced pressure to give 3.8 g of trans-3-[2-chloro-3,3,3-trifluoropropenyl]-2,2-dimethylcyclopropanecarbonyl chloride. The ir spectrum was consistent with the assigned structure.

Additional acid chlorides of formula III, prepared by the method illustrated in Example 5, are set forth as Examples 5.1 through 5.8 in Table III.

Examples 6 through 10 demonstrate the preparation of compounds of formula I in which R is —OR[1].

EXAMPLE 6

Synthesis of 3-Phenoxybenzyl-Trans-3-[2-Chloro-3,3,3-Trifluoropropenyl]-2,2-Dimethylcyclopropanecarboxylate To a stirred solution of 1.8 g (0.007 mole) of trans-3-]2-chloro-3,3,3-trifluoropropenyl]-2,2-dimethylcyclopropanecarbonyl chloride in 10 ml of methylene chloride at ambient temperature was added a solution of 1.6 g (0.008 mole) of 3-phenoxybenzyl alcohol and 0.73 g (0.009 mole) of pyridine in 5 ml of methylene chloride. Upon complete addition the reaction mixture was stirred at ambient temperature for 3 hours, then poured into 50 ml of water. The organic layer was separated, and the aqueous layer was extracted with three portions of 50 ml each of methylene chloride. The combined extracts were dried with sodium sulfate, filtered, and the filtrate evaporated under reduced pressure to a residual oil. Volatile components were removed from the oil at 125° C./0.05 mm using a Kugelrohr distillation system. The pot residue was determined 99% 3-phenoxybenzyl trans-3-[2-chloro-3,3,3-trifluoropropenyl]-2,2-dimethylcyclopropanecarboxylate, as determined by gas chromatographic analysis. The weight of product was 2.0 g. The nmr and ir spectra were consistent with the assigned structure.

Analysis calc'd for $C_{22}H_{20}ClF_3O_3$: C 62.05 H 4.73; Found: C 62.29 H 4.80.

EXAMPLE 7

Synthesis of α-Cyano-3-Phenoxybenzyl Trans-3-[2-Chloro-3,3,3-Trifluoropropenyl]-2,2-Dimethylcyclopropanecarboxylate This compound was prepared in the manner of Example 6 using 1.8 g (0.007 mole) of trans-3-[2-chloro-3,3,3-trifluoropropenyl]-2,2-dimethylcyclopropanecarbonyl chloride, as prepared in Example 4, 1.7 g (0.008 mole) of α-cyano-3-phenoxybenzyl alcohol, and 0.73 g (0.009 mole) of pyridine in 15 ml of methylene chloride. The pot residue analyzed 98.9% α-cyano-3-phenoxybenzyl trans-3-[2-chloro-3,3,3-trifluoropropenyl]-2,2-dimethylcyclopropanecarboxylate, as determined by gas chromatographic analysis. The weight of product was 2.4 g. The nmr and the ir spectra were consistent with the assigned structure.

Analysis calc'd for $C_{23}H_{19}ClF_3NO$: C 61.27 H 4.25; Found: C 61.57 H 4.38.

EXAMPLE 8

SYNTHESIS OF 3-PHENOXYBENZYL CIS,TRANS-3-[2-CHLORO-3,3,3-TRIFLUOROPROPENYL]-2,2-DIMETHYLCYCLOPROPANECARBOXYLATE

This compound was prepared in the manner of Example 6 using 1.8 g (0.006 mole) of cis,trans-3-[2-chloro-3,3,3-trifluoropropenyl]-2,2-dimethylcyclopropanecarbonyl chloride from Example 4, 1.4 g (0.007 mole) of 3-phenoxybenzyl alcohol, and 0.66 g (0.008 mole) of pyridine in 15 ml of methylene chloride. The pot residue analyzed 99% 3-phenoxybenzyl cis,trans-3-[2-chloro-3,3,3-trifluoropropenyl]-2,2-dimethylcyclopropanecarboxylate, as determined by gas chromatographic analysis. The weight of product was 1.0 g. The nmr and ir spectra were consistent with the assigned structure.

Analysis calc'd for $C_{22}H_{20}ClF_3O_3$: C 62.01 H 4.49; Found: C 62.11 H 4.58.

EXAMPLE 9

SYNTHESIS OF α-CYANO-3-PHENOXYBENZYL CIS,TRANS-3-[2-CHLORO-3,3,3-TRIFLUOROPROPENYL]-2,2-DIMETHYLCYCLOPROPANECARBOXYLATE

This compound was prepared in the manner of Example 6 using 1.8 g (0.006 mole) of cis,trans-3-[2-chloro-3,3,3-trifluoropropenyl]-2,2-dimethylcyclopropanecarbonyl chloride from Example 4, 1.6 g (0.007 mole) of α-cyano-3-phenoxybenzyl alcohol, and 0.66 (0.008 mole) of pyridine in 15 ml of methylene chloride. The pot residue analyzed 99% α-cyano-3-phenoxybenzyl cis,trans-3-[2-chloro-3,3,3-trifluoropropenyl]-2,2-dimethylcyclopropanecarboxylate, as determined by gas chromatographic analysis. The weight of product was 0.9 g. The nmr and ir spectra were consistent with the assigned structure.

Elemental analysis calc'd for $C_{23}H_{19}ClF_3NO_3$: C 61.46 H 4.26; Found: C 61.47 H 4.48.

The compounds of this invention may also be prepared by reacting a diene of the formula

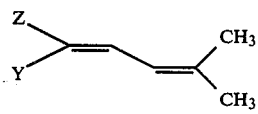

wherein Y and Z are defined above with diazoacetic esters of the formula $N_2CHCO_2R$ were R is lower alkyl or R' as defined above. The following example is illustrative of this method of preparation.

EXAMPLE 10

SYNTHESIS OF 3-PHENOXYBENZYL CIS,TRANS-3-[2-TRIFLUOROMETHYL-1-PROPENYL]-2,2-DIMETHYLCYCLOPROPANECARBOXYLATE

A. Synthesis of (3-methyl-2-butenyl)triphenylphosphonium chloride

A stirred solution of 52.3 g (0.5 mole) of 3-methyl-2-butenyl chloride and 144.1 g (0.55 mole) of triphenylphosphine in 400 ml of toluene was heated at 100° C. for 18 hours. The white solid formed was collected by filtration to give 147.6 g of (3-methyl-2-butenyl)triphenylphosphonium chloride.

B. Synthesis of 2-methyl-5-trifluoromethyl-2,4-hexadiene

A stirred solution of 144.3 g (0.39 mole) of (3-methyl-2-butenyl)triphenylphosphonium cloride in 300 ml of methylene chloride, under nitrogen atmosphere, was cooled to 0° C. To this cold solution a solution of 84.2 g (0.39 mole) of sodium methoxide 25% in methanol was added dropwise at a rate to keep the reaction mixture temperature below 4° C. Upon complete addition (40 minutes) a solution of 50.4 g (0.45 mole) of 1,1,1-trifluoroacetone in 5 ml of methylene chloride was added dropwise at a rate to keep the reaction mixture temperature below 6° C. Upon complete addition (40 minutes) the reaction mixture was allowed to warm to ambient temperature and was then stirred for 18 hours. The reaction mixture was washed twice with 150 ml portions of water, then dried with magnesium sulfate. The mixture was filtered and the filtrate concentrated by distillation. Pentane was added to the pot residue to precipitate triphenylphosphine oxide. The mixture was filtered and the filtrate concentrated by distillation. Diglyme was added to the pot residue, and an additional amount of triphenylphosphene oxide was collected by filtration. The filtrate was fractionally distilled by a spinning band distilling system to give in sixteen fractions 14.2 g of 98% 2-methyl-5-trifluoromethyl-2,4-hexadiene; b.p. 122°–124° C. The nmr spectrum was consistent with the assigned structure.

C. Synthesis of ethyl cis,trans-3-[2-trifluoromethyl-1-propenyl]-2,2-dimethylcyclopropanecarboxylate To a stirred solution of 11.9 g (0.073 mole) of 2-methyl-5-trifluoromethyl-2,4-hexadiene and 80 ml of rhodium diacetate, prepared in the manner of Mitchell, Rempel, et al., JCS A, 3322 (1970), under a nitrogen atmosphere, 8.3 g (0.073 mole) of ethyl diazoacetate was added by means of a syringe. Complete addition required 16.5 hours, due to the vigorous evolution of nitrogen. Upon complete addition the reaction mixture was stirred for 30.5 hours. Gas chromatographic analysis (GC) of the reaction mixture indicated it to contain 44% hexadiene starting materials. An additional 6.5 g of ethyl diazoacetate was added dropwise during an 18 hour period. GC analysis of the reaction mixture at the end of 60 hours indicated it to contain 20% hexadiene starting material. The reaction mixture was distilled under reduced pressure (5–12 mm) to give 10.2 g of crude product; b.p. 80°–85° C./5 mm. The crude product was placed on a chromatographic column of 300 g of silica gel. Elution was accomplished first with pure hexane, then with 3% ethyl acetate in hexane. The chromatography was completed in twenty fractions of 75 or 150 ml each. Appropriate fractions were analyzed by GC and nuclear magnetic resonance (NMR). NMR analysis indicated fraction 9 to be pure cis, E,Z isomers, and fractions 10–12 to be pure cis,trans isomers. Fractions 9–12 were combined to give 4.3 of ethyl cis,trans-3-[2-trifluoromethyl-1-propenyl]-2,2-dimethylcyclopropanecarboxylate.

D. Synthesis of 3-phenoxybenzyl cis,trans-3-[2-trifluoromethyl-1-propenyl]-2,2-dimethylcyclopropanecarboxylate A stirred mixture of 4.2 g (0.017 mole) of ethyl cis, trans-3-[2-trifluoromethyl-1-propenyl]-2,2-dimethylcyclopropanecarboxylate, 5.0 g (0.025 mole) of 3-phenoxybenzyl alcohol, and 3 drops of titanium isopropylate in 6 ml of nonane, under nitrogen atmosphere, was heated at 140° C. for 67 hours in a reaction vessel fitted with short-path distilling head for the removal of the by-product ethanol. GC analysis of the resulting reaction mixture indicated the reaction had gone to near completion. The reaction mixture was placed on a chromatographic column of 300 ml of silica gel in hexane. Elution was accomplished with 1 liter of 3% ethyl acetate in hexane followed by 5% ethyl acetate in hexane. Fractions 1 through 4 were each 500 ml in size. Fraction size was cut to 250 ml in Fractions 5 through 9. Fractions 4 and 5 were combined and distilled using a Kugelrohr distilling system, first at 95° C./0.05 mm to remove low boiling impurities, then at 105° C./0.05 mm to give 5.6 g of 3-phenoxybenzyl cis,trans-3-[2-trifluoromethyl-1-propenyl]-2,2-dimethylcyclopropanecarboxylate.

The ir and nmr spectra were consistent with the assigned structure.

Analyses calc'd for $C_{23}H_{23}F_3O_3$: C 68.31; H 5.73; Found: C 68.21; H 5.85.

The insecticidal compounds of this invention, prepared in accordance with the foregoing examples, are shown in Table IV below.

In the method aspect of this invention an effective insecticidal amount of the compound is applied to the locus where insect control is desired, e.g., to the insect itself or to the foliage or seeds of agricultural plants. The compounds are useful for the control of household, veterinary, and crop insects and may be applied as technical material or as a formulated product. Typical formulations include compositions of the active ingredient in combination with an agriculturally acceptable carrier or extender, preferably with a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. An agriculturally acceptable carrier may comprise about 99.5% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight. Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, etc.

In applying these compounds, whether alone or with other agricultural chemicals, an effective insecticidal amount of the active ingredient must be applied. While the application rate will vary widely depending on the choice of compound, the formulation and mode of application, the plant species being protected, and the planting density, a suitable use rate may be in the range of 0.005 to 3 kg./hectare, preferably 0.01 to about 1 kg./hectare.

The compounds of this invention were tested for initial insecticidal activity as described below.

EXAMPLE 11

Initial Contact Activity: The test compound was dissolved in a small amount of acetone, and the acetone solution was dispersed in water containing one drop of isooctylphenyl polyethoxyethanol to make a solution having 1250 ppm (w/w) or 512 ppm (w/w) active ingredient. Aliquots of this solution were diluted with an appropriate amount of water to provide solutions containing various concentrations of active ingredient. Test organisms and techniques were as follows: the activity against Mexican bean bettle (*Epilachna varivestis* Muls.) and southern armyworm (*Spodoptera eridania* [Cram.]) was evaluated by dipping the leaves of pinto bean plants into the test solution or spraying with the test solution and infesting the leaves with the appropriate immature-form insects after the foliage had dried. The activity against the pea aphid (*Acyrthosiphon pisum* [Harris]) was evaluated on broad bean plants whose leaves were dipped or sprayed before infestation with adult aphids. The activity against twospotted spider mites (*Tetranychus urticae* [Koch]) was evaluated on pinto bean plants whose leaves were dipped or sprayed with test solution after infestation with adult mites. The activity against the milkweed bug (*Oncopeltus faciatus* [Dallas]) and the plum curculio (*Conatrachelus nenuphar* [Herbst]) was evaluated by spraying the test solutions into glass dishes or jars containing the adult insects. Following application of the compound and infestation the tests were maintained in a holding room at 80° F. and 50% relative humidity for an exposure period of at least 48 hours. At the end of this time the dead and living insects or mites were counted, and the percent kill was calculated. Results of these tests are summarized in Table V. Table V also reports data at 156, 39 and 10 parts per million for the commercial insecticide permethrin, 3-phenoxybenzyl (±) cis,trans-3-(2,2-dichlorovinyl)-2,2-dimethylcyclopropane-1-carboxylate. The compounds in general exhibit excellent initial activity when compared with that of the reference compound.

EXAMPLE 12

The compounds of this invention were tested for insecticidal activity by applying to the insect appropriate amounts of a toxicant solution containing 5 mg/l of toxicant in acetone. The tests are read twenty-four hours after application of the toxicant solution and the percent kill determined. The well known commercial insecticide permethrin, 3-phenoxybenzyl (±) cis,trans-3-(2,2-dichlorovinyl)-2,2-dimethylcyclopropanecarboxylate, was used as the standard for comparison. Relative potency, based on a value of 1.0 for permethrin was determined by comparing percent kill for the test compound with that for the standard. The insects employed include southern armyworm (*Spodoptera eridania* [Cram.]), cabbage looper (*Trichoplusia ni* [Hubner]), beet armyworm (*Spodoptera exigua* [Hubner]), and corn earworm (*Heliothis zea* [Boddie]), Mexican bean bettle (*Epilachna varivestis* Muls.) and milkweed bug (*Oncopeltus faciatus* [Dallas]).

The results, shown in Table VI, demonstrate the insecticidal compounds of this invention are in general highly toxic against the organisms tested. Compounds incorporating the preferred Y and Z groups and the preferred alcohol residues (described above) were surprisingly active when compared with permethrin. These compounds are at least equivalent to permethrin in the tests and in most instances are superior.

The unexpected activity of the insecticides of this invention against aphids is illustrated in the example which follows:

EXAMPLE 13

In this example the actual aphid activity of certain compounds of the invention was compared with predicted values for these compounds. The predicted values were determined relative to permethrin using the formula:

$$\frac{\text{Lepidopterous Activity Permethrin}}{\text{Lepidopterous Activity Test Compound}} = \frac{\text{Aphid Activity Permethrin}}{\text{Predicted Aphid Activity Test Compound}}$$

The table below shows the application of this formula to two known compounds (A and B) to predict an expected aphid activity range, and that the actual observed activity for these two compounds is within or very close to the predicted range. Compound A is 3-phenoxybenzyl cis-3-(2,2-dichlorovinyl)-2,2-dimethylcyclopropane-1-carboxylate (~ 95% cis isomer). Compound B is α-cyano-3-phenoxybenzyl 3-(2,2-dichlorovinyl)-2,2-dimethylcyclopropane-1-carboxylate having ~ 40% cis isomer. This formula was then applied to certain compounds of this invention.

It was found that the actual $LC_{90}$ values for most of the test compounds was several times lower than the predicted value. For example, the formula predicts an $LC_{90}$ against aphids for compound 6.1 in the range of 27 to 32 parts per million. The actual observed value was 3 parts per million. Thus, this compound is about 10 times more active than one skilled in the art would predict. Similarly, compound 6.2 is 10 to 20 times more active than predicted, compound 6.3 is about 2 to 3 times more active than predicted, compound 6.8 is 45 to 65 times more active than predicted, etc. While some compounds, such as compounds 6.21 and 6.22, are not more active than predicted they show a substantial improvement over permethrin, thus demonstrating the unexpected aphicidal activity of the compounds of this invention.

PROJECTED AND OBSERVED APHICIDAL ACTIVITY

| Compound* | LD$_{50}$ Values (ng/insect) | | | LC$_{90}$ Values (ppm) - Aphids | |
|---|---|---|---|---|---|
| | SAW[1] | CL[2] | BAW[3] | Predicted Range | Observed Value |
| permethrin | 20 | 100 | 650 | — | 64 |
| A | 9 | 120 | 350 | 30–77 | 80 |
| B | 22 | 110 | 300 | 30–70 | 50 |
| 6.1 | 9 | 50 | 275 | 27–32 | 3 |
| 6.2 | 25 | 200 | 600 | 59–128 | 6 |
| 6.3 | 38 | 150 | 1100 | 96–122 | 40 |
| 6.8 | 10 | 50 | 230 | 23–32 | >0.5 |
| 6.9 | 14 | 53 | 260 | 26–45 | 1 |
| 6.10 | 19 | 70 | 380 | 38–61 | 40 |
| 6.15 | 12 | 33 | — | 21–38 | 5 |
| 6.17 | 11 | 83 | 232 | 24–53 | 12 |
| 6.21 | 1.6 | 8.5 | 27 | 3–5 | 6 |
| 6.22 | 3 | 12 | 82 | 8–10 | 32 |

*see Table IV for structure
[1]*Spodoptera eridania* [Cram.]
[2]*Trichoplusia ni* [Hubner]
[3]*Spodoptera exigua* [Hubner]

The example which follows illustrates the unexpected stability of certain compounds of this invention to photodegradation in the presence of light and air.

EXAMPLE 14

An emulsifiable concentrate formulation of α-cyano-3-phenoxybenzyl cis,trans-3-(2-chloro-3,3,3-trifluoropropenyl)-2,2-dimethylcyclopropanecarboxylate (compound 6.9) was diluted with toluene to give 220 mg of active ingredient per liter. One hundred μl aliquots were placed in each of six 5.0 cm diameter petri dishes, and the solvent allowed to evaporate leaving a residual deposit of 1.1 μg/cm$^2$. Three of the dishes were stored in the dark, and three were exposed to a 275 watt sunlamp at a distance of about 26 cm. After 24 hours, the residual deposit was recovered from each of the six plates, and was analyzed by high performance liquid chromatography for remaining active ingredient. The results for this compound, and also for compounds 6.1 and 6.16 of Table IV, are summarized below. Also included are results with permethrin and two additional compounds described by Elliott et al. in U.S. Pat. No. 4,024,163. The test compounds demonstrated a two-fold improvement over the reference compounds.

| Compound | % Remaining after 24 Hours | |
|---|---|---|
| | Dark | 275 watt sunlamp |
| 6.9 | 100 | 48.7, 43.5[a] |
| 6.1 | 100 | 41.1, 39.2[a] |
| 6.16 | 100 | 41.6 |
| permethrin | 100 | 19.1 |
| NRDC 148[b] | 100 | 21.2, 24.0[a] |
| NRDC 160[c] | 100 | 20.2 |

[a]Results of duplicated experiments, each done in triplicate
[b]cis isomeric component of permethrin
[c]cis isomeric component of α-cyano analog of permethrin

TABLE I

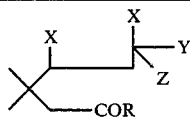

| Example | X | Y | Z | R |
|---|---|---|---|---|
| 1.1[a] | Br | CF$_3$ | Br | OCH$_3$ |
| 1.2[a] | Cl | CF$_3$ | F | OCH$_3$ |
| 1.3[a] | Cl | CF$_3$ | H | OCH$_3$ |
| 1.4[a] | Cl | CF$_2$Cl | Cl | OCH$_3$ |
| 1.5[a] | Cl | CF$_2$Cl | F | OCH$_3$ |
| 1.6[a] | Cl | CFCl$_2$ | F | OCH$_3$ |
| 1.7[a] | Cl | CF$_2$CF$_2$Cl | Cl | OCH$_3$ |
| 1.8[b] | Cl | C$_2$F$_5$ | Cl | OCH$_3$ |

[a]Boiling points (°C./mmHg): 1.1: 63/0.08; 1.2:71/0.09mm; 1.3: 112–115°/7; 1.4: 95–106/0.1–0.125; 1.5: 58–60/0.005; 1.6: 103/0.2–0.3; 1.7: 98–102/0.05.
[b]Structure confirmed by nmr.

TABLE II

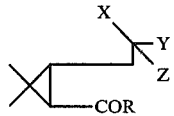

| Example | X | Y | Z | R |
|---|---|---|---|---|
| 2.1[a] | Br | CF$_3$ | Br | OCH$_3$ |
| 2.2 | Cl | CF$_3$ | F | OCH$_3$ |
| 2.3[b] | Cl | CF$_3$ | H | OCH$_3$ |
| 2.4 | Cl | CF$_2$Cl | Cl | OCH$_3$ |
| 2.5[a] | Cl | CF$_2$Cl | F | OCH$_3$ |
| 2.6 | Cl | CFCl$_2$ | F | OCH$_3$ |
| 2.7[b] | Cl | CF$_2$CF$_2$Cl | Cl | OCH$_3$ |

[a]Boiling points: (°C./mm Hg): 2.1: 100–113°/0.09–0.1; 2.5: 45–47°/0.02
[b]Structure confirmed by nmr

TABLE III

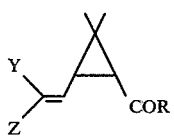

| Example | Y | Z | R | Isomer |
|---|---|---|---|---|
| 3.1[b] | CF$_3$ | Br | OCH$_3$ | c/t |
| 3.2[b] | CF$_3$ | F | OCH$_3$ | c/t |
| 3.3 | CF$_3$ | H | OCH$_3$ | c/t |
| 3.4[b] | CF$_2$Cl | Cl | OCH$_3$ | c/t |
| 3.5[b] | CF$_2$Cl | F | OCH$_3$ | c/t |
| 3.6[b] | CFCl$_2$ | F | OCH$_3$ | c/t |
| 3.7[b] | CF$_2$CF$_2$Cl | Cl | OCH$_3$ | c/t |
| 3.8[b] | C$_2$F$_5$ | Cl | OCH$_3$ | c/t |
| 4.1[c] | CF$_3$ | Br | OH | c/t |
| 4.2[d] | CF$_3$ | F | OH | c/t |
| 4.3[a] | CF$_3$ | H | OH | c/t |
| 4.4[a] | CF$_2$Cl | Cl | OH | c/t |
| 4.5[c] | CF$_2$Cl | F | OH | c |
| 4.6[c] | CF$_2$CF$_2$Cl | Cl | OH | c/t |
| 4.7 | C$_2$F$_5$ | Cl | OH | c/t |
| 5.1[e] | CF$_3$ | Br | Cl | c/t |
| 5.2[e] | CF$_3$ | F | Cl | c/t |
| 5.3[f] | CF$_3$ | H | Cl | c/t |
| 5.4[e] | CF$_2$Cl | Cl | Cl | c/t |
| 5.5[d,e] | CF$_2$Cl | F | Cl | c |
| 5.6[d,e] | CF$_2$CF$_2$Cl | Cl | Cl | c/t,Z |
| 5.7[b] | C$_2$F$_5$ | Cl | Cl | c/t,Z |
| 5.8[d,e] | CF$_3$ | Cl | Cl | c/t,E,Z |

[a]NMR spectrum consistent with assigned structure.
[b]Boiling points (°C./mm Hg): 3.1: 44–47°/0.07–0.08; 3.2: 71°/29; 3.4: 84–88°/1.-25–1.4; 3.5: 90–92°/11; 3.6: 60–71°/0.08; 3.7: 59–65°/0.07; 3.9: 98–110°/7; 5.7: 42–51°/0.1;
[c]Melting points (°C.): 4.1: 110–116°; 4.5: 80–87°; 4.6: 67–69°
[d]Structure confirmed by IR spectra
[e]Liquid, not isolated
[f]Semi-solid, not isolated

TABLE IV

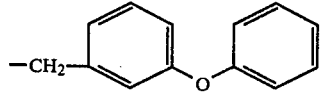

| Compound[a] | Y | Z | R¹ | Isomer |
|---|---|---|---|---|
| 6.1 | CF₃ | Cl | 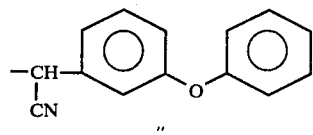 —CH₂—C₆H₄—O—C₆H₅ | c |
| 6.2 | CF₃ | Cl | " | c/t |
| 6.3 | CF₃ | Cl | " | t |
| 6.4 | CF₃ | Br | " | c |
| 6.5 | CF₃ | Br | " | c/t |
| 6.6 | CF₃ | Br | " | t |
| 6.7 | CF₃ | F | " | c |
| 6.8 | CF₃ | Cl | 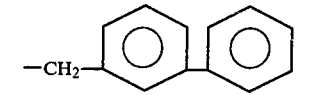 —CH(CN)—C₆H₄—O—C₆H₅ | c |
| 6.9 | CF₃ | Cl | " | c/t |
| 6.10 | CF₃ | Cl | " | t |
| 6.11 | CF₃ | Br | " | c/t |
| 6.12 | CF₃ | Br | " | t |
| 6.13 | CF₃ | F | " | c* |
| 6.14 | CF₃ | F | " | c* |
| 6.15 | CF₃ | F | " | t |
| 6.16 | CF₃ | Cl | 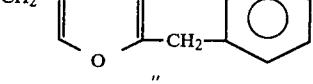 —CH₂-naphthyl | c |
| 6.17 | CF₃ | Br | " | c |
| 6.18 | CF₃ | Br | " | t |
| 6.19 | CF₃ | F | " | c |
| 6.20 | CF₃ | F | " | t |
| 6.21 | CF₃ | Cl | 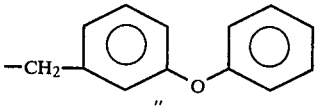 furan-CH₂—C₆H₅ | c |
| 6.22 | CF₃ | Cl | " | c/t |
| 6.23 | CF₂Cl | Cl | 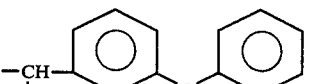 —CH₂—C₆H₄—O—C₆H₅ | c |
| 6.24 | CF₂Cl | F | " | c |
| 6.25 | CFCl₂ | F | " | c |
| 6.26 | C₂F₅ | Cl | " | c |
| 6.27 | CF₂CF₂Cl | Cl | " | c/t |
| 6.28 | CF₃ | H | " | c |
| 6.29 | CF₃ | φ | " | c |
| 6.30 | CF₃ | CH₃ | " | c/t |
| 6.31 | CF₃ | CF₃ | " | c/t |
| 6.32 | CF₂Cl | Cl | 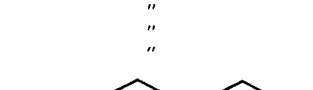 —CH(CN)—C₆H₄—O—C₆H₅ | c |
| 6.33 | CF₂Cl | F | " | c |
| 6.34 | C₂F₅ | Cl | " | c |
| 6.35 | CF₂CF₂Cl | Cl | " | c/t |
| 6.36 | CF₃ | H | " | c |
| 6.37 | CF₃ | H | " | t |
| 6.38[b] | CF₂Cl | Cl | 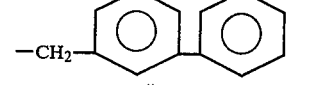 —CH₂-naphthyl | c |
| 6.39[b] | CF₂Cl | F | " | c |
| 6.40 | C₂F₅ | Cl | " | c |
| 6.41[d] | CF₂CF₂Cl | Cl | " | c |
| 6.42 | CF₃ | H | " | c |

TABLE IV-continued
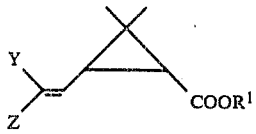
| Compound[a] | Y | Z | R[1] | Isomer |
|---|---|---|---|---|
| 6.43 | CF$_3$ | Cl | 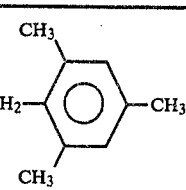 | c/t |
| 6.44 | CF$_3$ | Cl | 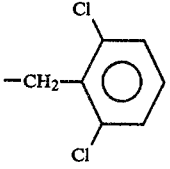 | t |
| 6.45 | CF$_3$ | Cl | 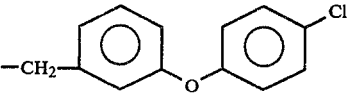 | c/t |
| 6.46 | CF$_3$ | Cl | 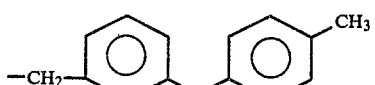 | c/t |
| 6.47 | CF$_3$ | Cl | 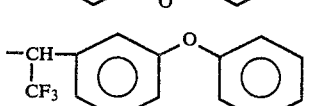 | c/t |
| 6.48 | CF$_3$ | Cl | 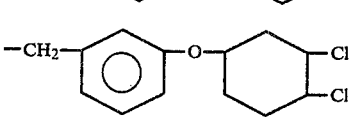 | c/t |
| 6.49 | CF$_3$ | Cl | 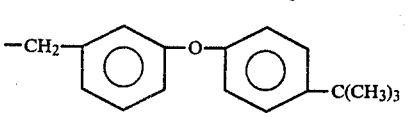 | c/t |
| 6.50 | CF$_3$ | Cl | 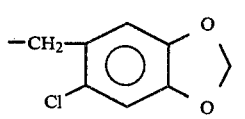 | c/t |
| 6.51 | CF$_3$ | Cl | 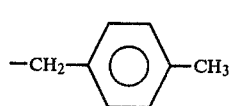 | c/t |
| 6.52 | CF$_3$ | Cl | 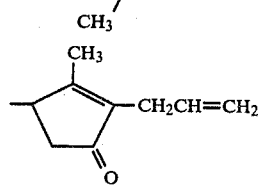 | c/t |
| 6.53 | CF$_3$ | Cl | 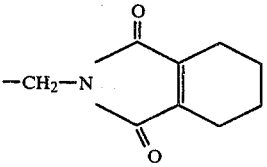 | c/t |

TABLE IV-continued

| Compound[a] | Y | Z | R[1] | Isomer |
|---|---|---|---|---|
| 6.54 | CF₃ | Cl | (bicyclic aromatic with Br) | c |
| 6.55 | CF₃ | Cl | (bicyclic aromatic) | c |
| 6.56 | CF₃ | Cl | (bicyclic aromatic with OCH₃) | c |
| 6.57 | CF₃ | Cl | (bicyclic aromatic with φ) | c |
| 6.58 | CF₃ | Cl | (bicyclic aromatic with NO₂) | c |
| 6.59 | CF₃ | Cl | (bicyclic aromatic) | c |

*Separated diastereoisomers  
[a]Assigned structure confirmed by nmr and elemental analysis  
[b]Bp 100°–102° C./0.005mm Hg  
[c]Bp 110° C./0.9mm Hg  
[d]NMR analysis only

TABLE V

INITIAL ACTIVITY — PERCENT KILL

| Compound[a] | Conc.[b] | MWB[1] | MBB[2] | SAW[3] | PA[4] | SM[5] | PC[6] |
|---|---|---|---|---|---|---|---|
| 6.1 | 39 | 6 | 100 | 100 | 70 | 87 | 100 |
| 6.2 | 39 | 30 | 100 | 100 | 100 | 6 | 100 |
| 6.3 | 30 (10)[c] | 5 | (100)[c] | (100)[c] | 100 | 7 | 90 |
| 6.4 | 64 | — | 100 | 100 | 100 | 36 | — |
| 6.5 | 78 | 40 | 100 | 100 | 100 | 54 | — |
| 6.6 | 64 | — | 100 | 100 | 100 | 0 | — |
| 6.7 | 20 | 40 | 100 | 100 | 100 | 85 | 50 |
| 6.8 | 39 | 90 | 100 | 100 | 100 | 41 | 15 |
| 6.9 | 39 | 90 | 100 | 100 | 100 | 15 | 45 |
| 6.10 | 39 (2.5) | 75 | (100) | (100) | (92) | 36 | 100 |
| 6.11 | 78 | 100 | 100 | 100 | 100 | 17 | — |
| 6.12 | 64 | — | 100 | 100 | 100 | 53 | — |
| 6.14 | 78 | 50 | 100 | 100 | 100 | 92 | 1 |
| 6.16 | 20 (39) | 10 | 100 | 100 | 100 | (50) | 10 |
| 6.17 | 64 | — | 100 | 100 | 100 | 0 | — |
| 6.18 | 64 (512) | — | 95 | 100 | 71 | (0) | — |
| 6.19 | 78 (5) | 41 | (100) | (100) | 100 | 100 | 55 |
| 6.21 | 64 | — | 100 | 100 | 100 | 0 | — |
| 6.22 | 64 | — | 100 | 100 | 100 | 0 | — |
| 6.23 | 78 | 45 | 100 | 100 | 100 | 100 | 5 |
| 6.24 | 20 | 70 | 100 | 100 | 100 | 29 | 10 |
| 6.26 | 20 | 100 | 100 | 82 | 100 | 100 | 20 |
| 6.27 | 78 (312) | 10 | 100 | 10 | 100 | 29 | (40) |
| 6.28 | 78 | 25 | 100 | 100 | 100 | 96.5 | 5 |
| 6.29 | 64 | — | 100 | 5 | 0 | 0 | — |
| 6.30 | 64 | — | 100 | 100 | 100 | 48 | — |
| 6.31 | 64 (512) | — | 100 | 65 | 100 | (0) | — |
| 6.32 | 78 (20) | 10 | 100 | 100 | 0(55) | 0 | 0 |
| 6.33 | 78 | 100 | 100 | 100 | 100 | 42 | 10 |
| 6.35 | 78 (312) | 30 | 100 | 100 | 100 | 18 | (25) |
| 6.39 | 78 | 95 | 100 | 100 | 100 | 94 | 25 |
| 6.40 | 78 | 25 | 100 | 100 | 100 | 80 | 0 |
| 6.41 | 78 (312) | 10 | 100 | 100 | 90 | 58 | (0) |
| 6.42 | 78 | 55 | 100 | 100 | 90 | 92 | 0 |
| 6.43 | 20 (312) | 5 | 100 | 100 | 92 | (31) | — |
| 6.44 | 20 (312) | 10 | 95 | 100 | 100 | 19 | — |
| 6.45 | 78 | 22 | 100 | 100 | 100 | — | 15 |
| 6.46 | 78 | 10 | 100 | 100 | 100 | — | 15 |
| 6.47 | 78 | 5 | 100 | 100 | 100 | — | 5 |
| 6.48 | 39 | 0 | 100 | 28 | 90 | 0 | 0 |
| 6.49 | 39 | 10 | 100 | 0 | 0 | 0 | 0 |
| 6.50 | 64 | — | 65 | 100 | 65 | 0 | — |
| 6.51 | 64 | — | 45 | 0 | 0 | 0 | — |
| 6.52 | 64 | — | 45 | 20 | 0 | 0 | — |
| 6.53 | 64 | — | 100 | 30 | 0 | 0 | — |
| 6.55 | 512 | — | 100 | 100 | 43 | 0 | — |
| 6.56 | 512 | — | 85 | 100 | 100 | 0 | — |
| 6.57 | 512 | — | 100 | 100 | 100 | 0 | — |
| 6.58 | 64 | — | 100 | 100 | 50 | 65 | — |
| 6.59 | 64 | — | 80 | 0 | 20 | 0 | — |
| permethrin | 156 | 71 | — | — | 94 | 36 | 100 |
|  | 39 | 30 | 100 | 100 | 93 | — | 33 |
|  | 10 | 10 | 75 | 100 | 94 | — | 15 |

TABLE V-continued

| Compound[a] | Conc.[b] | INITIAL ACTIVITY PERCENT KILL | | | | | |
|---|---|---|---|---|---|---|---|
| | | MWB[1] | MBB[2] | SAW[3] | PA[4] | SM[5] | PC[6] |
| CHECK[d] | — | 0 | 0 | 5 | 10 | 0 | 0 |

[a] Structure in Table IV
[b] Concentration in parts per million
[c] Data in parenthesis taken at concentration shown in parenthesis
[d] Untreated sample
[1] *Oncopeltus faciatus* [Dallas]
[2] *Epilachna varivestis* Muls.
[3] *Spodoptera eridania* [Cram.]
[4] *Acyrthosiphon pisum* [Harris]
[5] *Tetranychus urticae* [Koch]
[6] *Conatrachelus nenuphar* [Herbst]

TABLE VI

| Compound* | Relative Potency Against | | | | | |
|---|---|---|---|---|---|---|
| | SAW[1] | CL[2] | BAW[3] | CEW[4] | MBB[5] | MWB[6] |
| 6.1 | 2.3–2.6 | 1.0–2.7 | 1.9–2.8 | 1.5–1.8 | 7.1 | 2.4 |
| 6.2 | 0.9–1.0 | 0.5–0.9 | 1.0 | 1.2 | — | — |
| 6.3 | 0.5–0.7 | 0.7–1.1 | 0.6 | 0.9 | — | — |
| 6.4 | 2.5 | 3.4 | 1.3 | — | 5.1 | 4.9 |
| 6.5 | 1.8 | 1.1 | 1.5 | 1.0 | — | — |
| 6.6 | 0.1 | 0.5 | 0.6 | — | 0.4 | 1.5 |
| 6.7 | 2.4 | 1.8 | 1.3 | — | — | — |
| 6.8 | 2.1–2.3 | 2.1–3.0 | 2.5 | 1.8 | — | — |
| 6.9 | 1.4–1.9 | 2.4–3.6 | 2.1 | | 6.0 | 5.6 |
| 6.10 | 1.0–1.7 | 1.8–2.0 | 1.7 | 2.0 | — | — |
| 6.11 | 1.3 | 1.7 | 1.8 | 1.1 | — | — |
| 6.12 | 0.01 | — | — | — | 1.88 | 1.6 |
| 6.13 | 0.6 | 3.1 | — | — | — | — |
| 6.14 | 0.3 | 0.1 | — | — | — | — |
| 6.15 | 1.7 | 3.0 | — | — | — | — |
| 6.16 | 1.0 | 0.8 | 1.6 | 0.7 | 0.7 | 3.6 |
| 6.17 | 1.8 | 1.7 | 2.8 | — | 1.6 | 6.6 |
| 6.18 | 0.1 | 0.06 | — | — | — | — |
| 6.19 | 0.9 | 0.5 | — | — | — | — |
| 6.20 | 0.08 | <0.001 | — | — | — | — |
| 6.21 | 12.2 | 11.8 | 24.1 | — | 7.9 | 67.6 |
| 6.22 | 6.4 | 8.2 | 7.9 | — | 3.8 | 55.7 |
| 6.23 | 0.6 | 0.8 | — | — | — | — |
| 6.24 | 1.1 | 0.4 | — | — | — | — |
| 6.25 | 0.1 | 0.1 | — | — | — | — |
| 6.26 | 0.02 | 0.1 | 0.2 | 0.1 | — | — |
| 6.27 | 0.01 | 0.6 | — | — | — | — |
| 6.28 | 0.5 | 0.3 | — | — | — | — |
| 6.29 | <0.001 | <0.001 | — | — | 0.1 | <0.001 |
| 6.30 | 0.9 | 1.0 | — | — | — | — |
| 6.31 | .06 | <0.001 | — | — | — | — |
| 6.32 | 0.04 | <0.001 | — | — | — | — |
| 6.33 | 0.4 | 0.3 | — | — | — | — |
| 6.34 | 0.08 | 0.2 | — | — | — | — |
| 6.35 | 0.04 | 0.05 | — | — | — | — |
| 6.36 | 0.3 | 0.2 | — | — | — | — |
| 6.37 | 0.8 | 0.5 | — | — | — | — |
| 6.38 | 1.3–1.6 | 0.9 | — | — | — | — |
| 6.39 | 0.4 | 0.1 | — | — | — | — |
| 6.40 | 0.03 | <0.001 | — | — | — | — |
| 6.41 | 0.01 | <0.001 | — | — | — | — |
| 6.42 | 0.1 | <0.001 | — | — | — | — |
| 6.43 | 0.08 | 0.09 | — | — | — | — |
| 6.44 | 0.2 | 0.05 | — | — | — | — |
| 6.45 | 0.2 | 0.6 | — | — | — | — |
| 6.46 | 0.05 | 0.3 | — | — | — | — |
| 6.47 | 0.06 | 0.05 | — | — | — | — |
| 6.48 | <0.001 | <.001 | — | — | — | — |
| 6.49 | <0.001 | <.001 | — | — | — | — |
| 6.50 | 0.06 | — | — | — | 0.06 | 0.6 |
| 6.51 | 0.05 | — | — | — | 0.01 | 0.4 |
| 6.52 | 0.01 | — | — | — | 1.0 | 0.07 |
| 6.53 | 0.04 | — | — | — | 0.5 | <0.001 |
| 6.54 | 0.05 | 0.06 | — | — | — | — |
| 6.55 | 0.03 | 0.04 | — | — | — | — |
| 6.57 | 0.01 | — | — | — | — | — |
| 6.58 | 0.4 | 0.2 | — | — | — | — |
| 6.59 | 0.2 | 0.2 | — | — | — | — |

[1] *Spodoptera eridania* [Cram.]
[2] *Trichoplusia ni* [Hubner]
[3] *Spodoptera exiqua* [Hubner]
[4] *Heliothis zea* [Boddie]
[5] *Epilachna varivestis* Muls.
[6] *Oncopeltus facintus* [Dallas]
*See Table IV for structure

I claim:

1. A compound of the formula

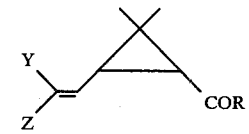

wherein one of Y and Z is trihalomethyl and the other is halogen and R is —OR[1] where R[1] is represented by the formula

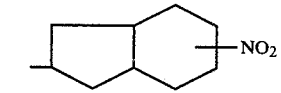

2. The compound of claim 1 wherein R[1] is

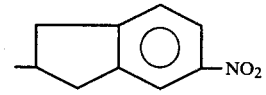

3. A method for insect control which comprises applying to the locus where control is desired an insecticidally effective amount of the compound of claim 1 or 2.

* * * * *

UNITED STATES PATENT AND TRADEMARK OFFICE
CERTIFICATE OF CORRECTION

PATENT NO. : 4,243,677

DATED : January 6, 1981

INVENTOR(S) : John F. Engel

It is certified that error appears in the above—identified patent and that said Letters Patent is hereby corrected as shown below:

Column 7, Example 6, line 36, "]2-chloro" should read --[2-chloro--. Column 8, line 8, "$C_{23}H_{19}ClF_3NO$" should read --$C_{23}H_{19}ClF_3NO_3$--; Example 9, line 44, after "0.66" insert --g--; line 66, "were" should read --where--. Columns 15-16, Table IV, Compound 6.21, the formula should read as follows:

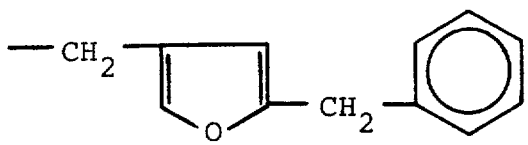

UNITED STATES PATENT AND TRADEMARK OFFICE
CERTIFICATE OF CORRECTION

PATENT NO. : 4,243,677
DATED : January 6, 1981
INVENTOR(S) : John F. Engel

It is certified that error appears in the above—identified patent and that said Letters Patent is hereby corrected as shown below:

Columns 17-18, Table IV, Compound 6.48, the formula should read as follows:

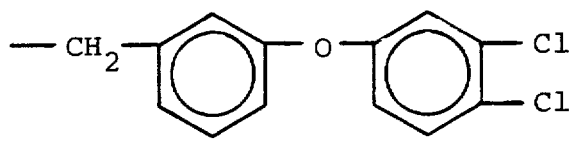

Columns 19-10, Table IV, Compound 6.57, under "Isomer" insert --c--. Column 20, Table V, last line under $PA^4_4$, "94" should read --54--. Column 22, Table VI, line 20, "exiqua" should read --exigua--.

UNITED STATES PATENT AND TRADEMARK OFFICE
CERTIFICATE OF CORRECTION

PATENT NO. : 4,243,677
DATED : January 6, 1981
INVENTOR(S) : John F. Engel

It is certified that error appears in the above—identified patent and that said Letters Patent is hereby corrected as shown below:

Claim 1, line 40, the formula should read as follows:

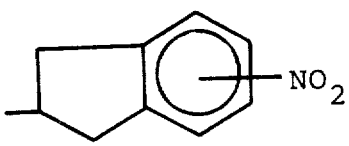

Signed and Sealed this

Twenty-sixth Day of February 1985

[SEAL]

Attest:

DONALD J. QUIGG

Attesting Officer

Acting Commissioner of Patents and Trademarks